(12) United States Patent
Barath

(10) Patent No.: US 7,008,436 B2
(45) Date of Patent: Mar. 7, 2006

(54) METHOD AND COUPLING APPARATUS FOR FACILITATING AN VASCULAR ANASTOMOSES

(76) Inventor: Peter Barath, 3 Hampton Dr., Oak Brook, IL (US) 60523

( * ) Notice: Subject to any disclaimer, the term of this patent is extended or adjusted under 35 U.S.C. 154(b) by 691 days.

(21) Appl. No.: 09/733,563

(22) Filed: Dec. 8, 2000

(65) Prior Publication Data
US 2002/0116016 A1 Aug. 22, 2002

(51) Int. Cl.
*A61B 17/04* (2006.01)

(52) U.S. Cl. .................................. 606/153; 606/155
(58) Field of Classification Search ............... 606/153, 606/155
See application file for complete search history.

(56) References Cited

U.S. PATENT DOCUMENTS 3,818,515 A * 6/1974 Neville .................. 606/153
4,352,358 A * 10/1982 Angelchik ............... 285/140.1
6,007,576 A * 12/1999 McClellan ............... 623/23.64
6,030,395 A * 2/2000 Nash et al. ............... 606/153
6,273,912 B1 * 8/2001 Scholz et al. ............. 623/1.1

* cited by examiner

Primary Examiner—Gary Jackson
(74) Attorney, Agent, or Firm—Michael E. Klicpera

(57) ABSTRACT

The present invention, which addresses the needs described above, resides in an apparatus and method for coupling vascular apertures to a blood supply vessel in a manner that minimizes the time and operator dependent inconsistency in performing vascular anastomoses. In the coronary setting, this concept is fast and can be applied to both conventional and minimally invasive operative techniques. In the preferred embodiment, the present invention relates to an apparatus and method for facilitating end-to-side vascular anastomoses procedure, whereby the present invention acts as a coupling apparatus between a first, blood supplying hollow organ, e.g. the LIMA, radial artery, or a saphenous vein and the side wall of second hollow organ, typically one of the major coronary arteries, such as the left coronary artery (LCA), right coronary artery (RCA) or the circumflex (CX).

48 Claims, 4 Drawing Sheets

US 7,008,436 B2

METHOD AND COUPLING APPARATUS FOR FACILITATING AN VASCULAR ANASTOMOSES

PRIOR APPLICATIONS

This invention was disclosed in a Disclosure Document numbered 448542 entitled "Anastomosis Coupling Apparatus" and submitted to the Patent and Trademark Office on Dec. 8, 1998.

FIELD OF THE INVENTION

This invention relates generally to the field of surgery and, more particularly, to a method and device for performing conventional or minimally invasive bypass surgery. More specifically, the present invention relates to a method and a device to perform end-to-side vasculature anastomoses with either conventional or minimally invasive methods coupling a conduit vein or artery with a normal segment of a coronary or other vessel distal to the diseased, narrowed segment.

BACKGROUND OF THE INVENTION

In the context of coronary vessel disease, the flow of oxygenated blood to the myocardium of the heart is inhibited by a stenosis or obstruction on one or more of the coronary arteries, Flow can be restored by providing a coronary artery bypass graft (CABG). In this procedure, connection is established between the aorta and a normal segment of the diseased coronary vessel using a free vein (e.g. saphenous vein) or arterial (e.g. radial) segment. Alternatively, a distal segment of an vessel (e.g. internal mammary, gastroepiploic etc) is mobilized, severed and attached to the coronary vessel. Both the free grafting and the mammary artery, gastroepiploic artery grafting can be performed during open chest surgery with or without cardiolpulmonary bypass ("on/off pump") or using less invasive ("minimally invasive") techniques, ultimately, thoracoscopy without opening the chest. One problem the surgeon faces during any of these above procedures is how to grab the bypassing vessel since the vessel with the interrupted blood flow becomes flabby and hard to handle, does not keep the preferred (i.e. a elongated ) shape to fit exactly the aperture on the target vessel. Also, the bypassing vessel needs extremely gentle handling to prevent even minimal damage that can lead to future proliferation and eventually, narrowing of either the vessel and/or that of the anastomosis. Acutely, rough handling of the live conduit artery (i.e. internal mammary artery) might lead irreversible spasm. Therefore, it is imperative to have an apparatus, which makes:

1) grabbing of the conduit vessel easy and less traumatic, 2) the anastomosis site of the bypassing or blood supplying vessel follows the desired shape, and 3) the proper sizing of the target aperture to mimic the size and configuration of the bypassing or blood supplying distal anastomosis aperture.

SUMMARY OF THE INVENTION

In general, the advantages of this concept is that a relatively fast and uniform method for facilitating the coupling of various conduits as an anastomoses procedure within various areas of the human body can be achieved. The present invention, which addresses the needs described above, resides in an apparatus and method for coupling vascular apertures to a blood supply vessel in a manner that minimizes the time and operator dependent inconsistency in performing vascular anastomoses. In the coronary setting, this concept is fast and can be applied to both conventional and minimally invasive operative techniques.

In the preferred embodiment, the present invention relates to an apparatus and method for facilitating end-to-side vascular anastomoses procedure, whereby the present invention acts as a coupling apparatus between a first, blood supplying hollow organ, e.g. the LIMA, radial artery, or a saphenous vein and the side wall of second hollow organ, typically one of the major coronary arteries, such as the left coronary artery (LCA), right coronary artery (RCA) or the circumflex (CX).

In one of many applications contemplated for the use of this coupling apparatus, the input end of an anastomosis coupling apparatus is secured the free mobile segment of a supplying vessel by means of an adhesive or glue, or may be attached with sutures or staples. The anastomosis coupling apparatus can be fitted with a means for controlling its location and configuration within a body cavity using standard incision technologies presently known by those skilled in the art.

The output end of the coupling apparatus is appropriately prepared for securement means by attachment with staples or sutures and in some cases, by means of additional adhesive or glue application to increase the security of the attachment. Then, the prepared coupling apparatus is positioned in close proximity to the desired anastomosis site on a coronary vessel and finally engaged to the coronary vessel site.

Now blood flow is established from the blood supplying vessel to the coronary distal to the obstruction, supplying the myocardial tissues once nourished by the native unoccluded vessel. All relatively trivial vascular, abdominal, or thoracotoic incisions made during the course of the procedure are treated according to standard practices. The patient is monitored for period of time to verify that the anastomosis has been successful and that no leakage is occurring from the joint.

The method and devices of the present invention find particular application for performing vascular anastomoses, including, in particular, coronary bypass between an arterial source and an obstructed coronary vessel. In particular, the method and devices of the present invention find particular application in establishing an anastomoses between the severed end of a supplying vessel e.g. the left internal mammary artery ("LIMA") and the side wall of a coronary artery e.g. the left anterior descending coronary artery ("LAD"), circumflex ("CX") or right coronary artery ("RCA").

DESCRIPTION OF THE PREFERRED EMBODIMENT

Figure 1:
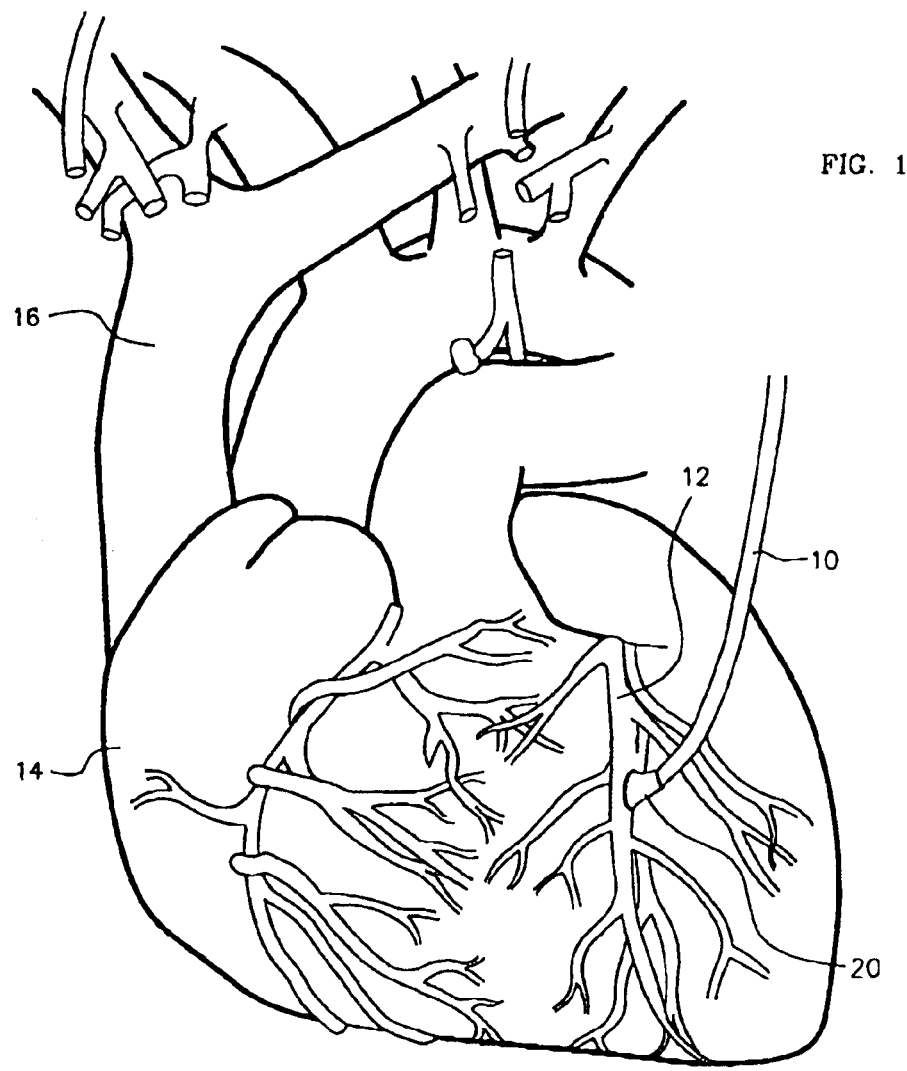
FIG. 1 is a schematic perspective view of a patient in undergoing a coronary bypass procedure, showing the placement and anastomosis coupling apparatus in accordance with the present invention.

The present invention can be used as a means to facilitate the anastomosis procedure and decrease the likelihood of leakage in conventional open-chest, small incision bypass surgeries on and off cardiopulmonary bypass. These procedures are well known by those skilled in the art and recitation of these procedures is not reproduced here.

Alternately, in closed chest thoracoscopic methods, the present invention can employed as describe herein. In preparation for the surgical procedure of the present invention, the patient is placed on the operating table in a supine position, and general anaesthesia administered. The patient is selectively intubated using conventional methods with a double-lumen endotracheal tube, thereby permitting the left lung to be deflated. The patient is then placed in a lateral decubitus position on his right side. Next, based upon the pathology and anatomy of the patient, the surgeon identifies a suitable position for insertion of a Beress insufflation needle or other suitable needle. Typically, this needle will be inserted between the fifth or sixth intercostal space along the anterior axillary line and into the region between the parietal pleura and the pericardium. The parietal pleura and pericardium are then separated by conventional gas dissection, and the Beress needle is removed.

In order to perform the anastomosis procedure, it is first desirable to visualize the coronary vessel using conventional angiographic techniques. Typically, the surgeon will already have an angiogram of the affected coronary vessel available as a result of the earlier diagnosis of the necessity for the coronary bypass. Similarly, it is desirable to use conventional angiographic techniques to visualize the arterial source. The location of the stenosis will dictate the proper placement of the secured anastomosis coupling apparatus.

For the purpose of an example, the following will define an embodiment that couples the LIMA to the LAD coronary artery. It is contemplated by the Applicant that supplying arteries other than the LIMA, freed segments of veins, radial and other vessels can be used with this apparatus invention and method. Furthermore, other coronary arteries, e.g. the RCA, Circumflex, can be used with this apparatus invention and method.

Under the guidance of the endoscopic telescope or conventional endoscopic instruments are used to isolate the a supply vessel from surrounding tissue and the chest wall. A number of considerations are taken into account in determining the site for severing the LIMA 10. Using the angiographic and direct visualization, the surgeon can determine a desirable proposed site for severing which will provide a suitable length of vessel with a diameter that closely matches that of the coronary vessel. A maximum length of the LIMA, 10 can be obtained by severing the LIMA 10 at its distal. end near the diaphragm. In preparation for severing, blood flow to the side branches of the LIMA 10 is interrupted by clipping or cauterizing the branches of the LIMA proximally of the proposed site for severing. Blood flow through the LIMA 10 is interrupted by applying an appropriate located clips. The LIMA 10 is then severed using conventional endoscopic techniques, thereby creating a proximal severed end and a distal severed end.

Using conventional endoscopic techniques, the parietal pleura is dissected and the pericardial sac is opened. The endoscopic telescope can be used to visualize the LAD 12 while the LAD 12 is then isolated endoscopically from the surrounding tissue proximally and distally of the proposed site for anastomosis.

With reference now to the exemplary drawings, and particularly to FIG. 1, there is shown a schematic perspective view of a patient who had undergone an artery-to-artery coronary bypass procedure in accordance with the present invention in which an end-to-side vascular anastomosis is established between the severed end of the a supply vessel, e.g. a by-pass graft or left internal mammary artery ("LIMA") 10 and the side-wall of a coronary artery e.g. left anterior descending coronary artery ("LAD") 12, distally to the site of an stenosis. In this figure, the input end of the anastomosis coupling apparatus is secured to a by-pass graft 10 and the output end of the coupling to the LAD 12 of the heart 14.

Figure 2:
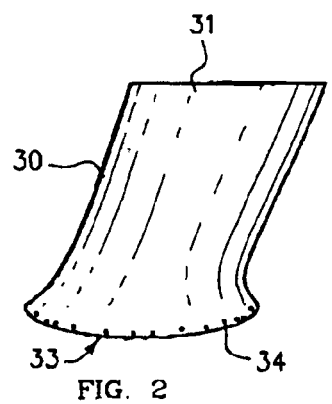
FIG. 2 is a lateral view of the first embodiment of the anastomosis coupling apparatus adapted for use in the coronary bypass procedure shown in FIG. 1.

As shown in FIG. 2, the first embodiment of the anastomosis coupling apparatus 30 includes a base edge 33 having a plurality of perforations 34. In this embodiment, the anastomosis coupling apparatus 30 can be fabricated from biocompatible polymers, such as polyurethanes, silicones, polyurethane/silicone copolymers, polyethylene, or nylon. Alternately, the anastomosis coupling apparatus 30 can be comprised of biocompatible metals, such as titanium or stainless steel. Furthermore, in some instances, it may be desirable that the anastomosis coupling apparatus degrade after the blood supplying vessel and coronary vessel have naturally secured themselves together. In this instance, common biocompatible and degradable materials, such as the poly-d,l-lactate (lactide), poly-d,l-lactate-glycolate will be used as the material for fabrication of the invention.

In the preferred process of forming the anastomosis coupling from a polymer or degradable material, conventional processes employing molds with various heat cycles appropriate for selected material, will be used to fabricate the apparatus. If the anastomosis coupling apparatus is fabricated from metal, conventional machining techniques will be employed.

The anastomosis coupling apparatus 30 can also be made in various sizes or configurations. In typically coronary applications, the coupling will range from an inside diameter between 0.5 mm to 10.0 mm, with a preferable range of 2.0 mm to 4.0 mm, depending on the overall diameter of the blood supplying vessel and the particular application. The inside diameter of the input end anastomosis coupling 30 must be large enough to accept a blood vessel within its inner cavity without imparting undue trauma or stress on the vessel. It can be appreciated that the exact inside diameter is of relative importance, as it must function to provide a secure bond between the inside surface of the anastomosis coupling and the outside surface of the bypassing or blood supplying vessel.

Also shown in this embodiment of the anastomosis coupling apparatus 30 is a proximal end 31 which is the input end that secures to the bypassing vessel for a blood supply. The distal end 33 has a lower rim 32 which has a plurality of perforations 34 used to facilitate securement to the aperture 42 of a coronary vessel 40 with either stitches and/or stables.

The anastomosis coupling 30 can also deviate from the configuration demonstrated in the Figures, whereby the overall configuration more closely resembles a "Y", "V", or "U" shape. Furthermore, the specifically configured anastomosis coupling 30 apparatus could have an acute angle between the longitudinal axis of the input end and the longitudinal axis of the output. In addition, the specifically configured anastomosis coupling apparatus 30 might have a right deflection angle between a right angle formed between the longitudinal axis of the input end and an axis parallel the lip of a distal end of the input end, wherein this deflection angle should be larger than 5 degrees. Also, the specifically configured anastomosis coupling apparatus can have a lip deflection angle between a right angle formed between the longitudinal axis the input end and an axis parallel the lip of a distal end of the input end, wherein this lip deflection angle is larger than 5 degrees.

Figure 3:
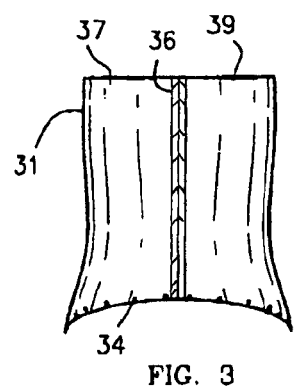
FIG. 3 is a posterior view of the anastomosis coupling apparatus showing a hinge mechanism.
Figure 4:
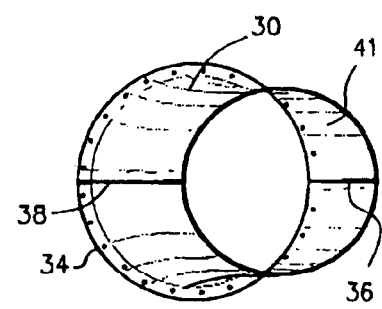
FIG. 4 is an angled superior view of the anastomosis coupling apparatus.
Figure 5:
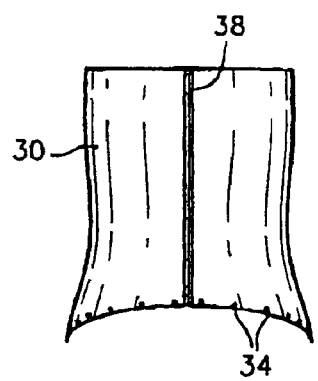
FIG. 5 is an anterior view of the anastomosis coupling apparatus showing a anterior opening or slot.

Now referring to FIGS. 3–5, it can be appreciated that the coupler comprises two halves, 37 and 39, connected by a hinge mechanism 36 located on the posterior side and separated apart from slot 38 located on anterior side. This "clam shell" design facilitates the proper placement of the supply vessel 10 within the inner cavity defined between the two coupler halves. The bypassing or blood supplying vessel should be positioned so that it exits the lower rim 33 with an elongated shape to fit the shape of the surgically opened aperture of the target coronary vessel.

The hinge mechanism 36 can comprise a simple indent or groove made in the polymer fabrication material, or a more complex arrangement in the metallic design.

Also, proper application of the adhesive or glue to outside surface of the blood supplying vessel and to the inside surface 41 of the anastomosis coupling apparatus 30 is accomplished much easier when separated.

Figure 6:
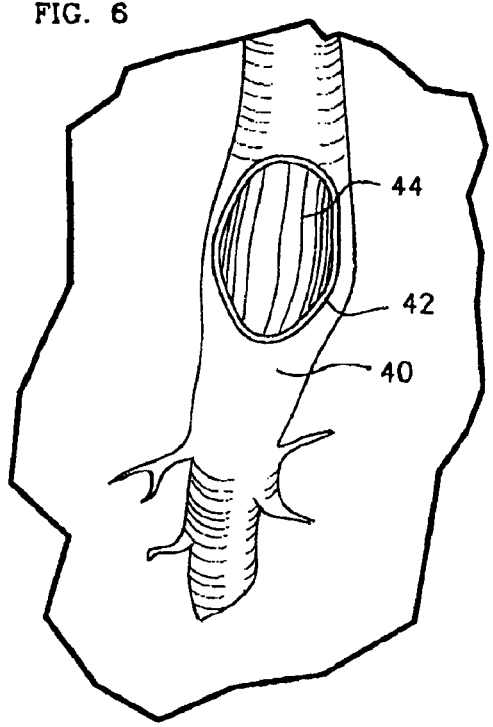
FIG. 6 is a perspective view showing a coronary vessel prepared for engagement with the anastomosis coupling apparatus.

Referring to FIG. 6, a target or coronary vessel 40 has been surgically prepared to create an aperture 42 and exposing vessel lumen 44. Blood flow is inhibited during this stage of the procedure by using a clamp or similar mechanism (not shown) to block blood flow. It is important that the operator use the size and dimensions of the bypassing or blood supplying vessel as a template in creating the aperture in the target vessel.

Figure 7:
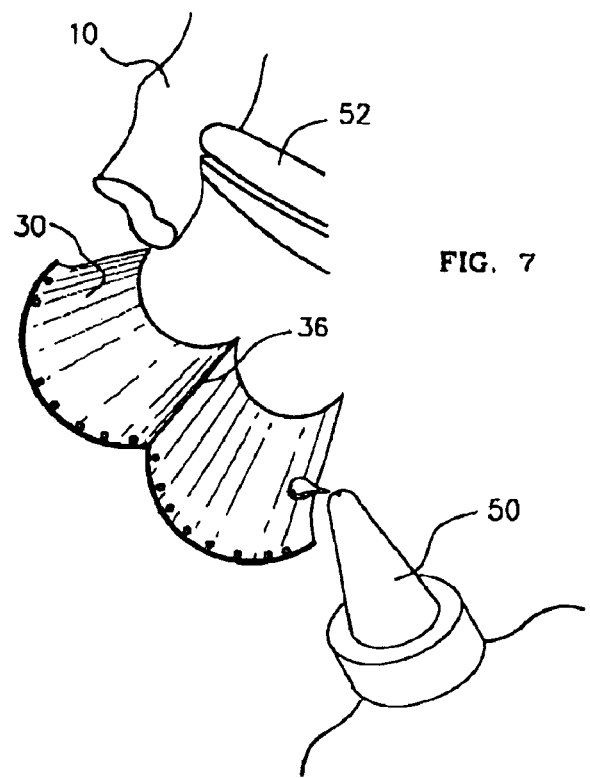
FIG. 7 is a perspective view of the coupling apparatus in an opened position and showing a representation of using an adhesive or gluing means applied between the outside surface of the severed end of the arterial source and inner surface of the anastomosis coupling apparatus thereby securing the two surfaces together.

In FIG. 7, the coupling apparatus 30 is shown in its opened configuration and being prepared for securing the bypassing or blood supply vessel 10 to the coupling apparatus 30. The operator can place the bypassing or blood supplying vessel 10 into the apparatus 30 without inflicting damage to the vessel 10 by using a pair of forceps 52. At this time, tissue glue or adhesive 50 is applied to the inner surface of the coupling apparatus 30 and around the bypassing or blood supplying vessel 10. The glue or adhesive 50 utilized to secure the severed end of the supply vessel to the side wall of the target vessel may be any biocompatible glue which gives sufficient strength to secure the outer surface of the supplying vessel 10 in engagement with the inner surface of the anastomosis coupler apparatus 30. Preferably, the glue is fast acting, so that the region may be secured expeditiously. Examples of such biocompatible glue are the fibrin glue sold under the trade name "TISSEEL" manufactured by Immuno-U.S., Inc. of New York and a gelatin-resorcine-formyl biological glue distributed by Laboratories Cardial. Then, by closing the two halves or releasing the opening force, the coupling apparatus 30 encloses the bypassing or blood supplying vessel 10 within its cavity, securing the vessel in place.

Figure 8:
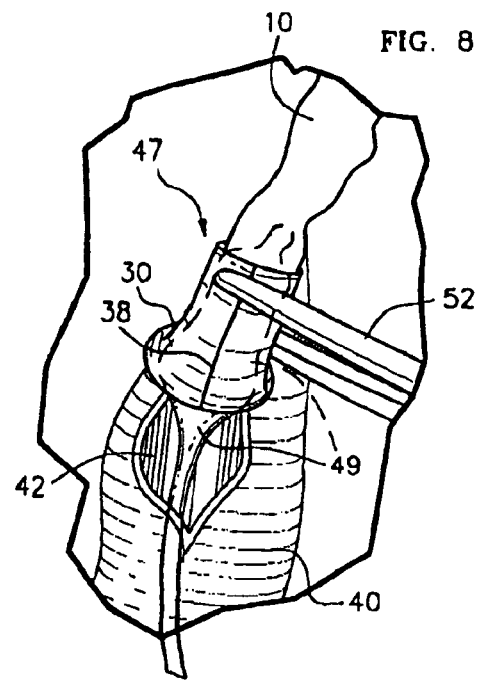
FIG. 8 is a perspective view showing the outside surface of the severed end of the supply arterial source and anastomosis coupling apparatus secured together. The engaged blood supplying source and anastomosis coupling apparatus are also shown being advanced toward the prepared coronary vessel for securement.

Now referring to FIG. 8, a highly complaint, (that matches the inside diameter of the supplying vessel) deflated pear-shaped balloon 49 is inserted into the distal lumen of the bypassed or blood supplying vessel 10 and inflated to a very low pressure. This process functions to assure that close engagement between the outside surface of the vessel 10 and the inside surface of the coupler apparatus 30, and even distribution of the adhesive, is achieved. The desired result is a firm and secure attachment between the two objects. The pear shaped balloon 49 assures that the bypassing or blood supplying vessel assumes the elongated shape of the apparatus 30. It is highly desirable to spread the distal end of the vessel 10 around the distally funnel-shaped aperture of the apparatus leaving a small excess from the vessel.

Figure 9:
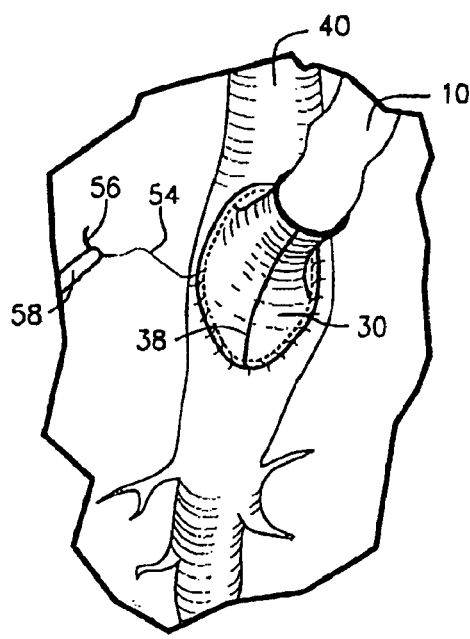
FIG. 9 is a perspective view of the blood supplying vessel and the anastomosis coupling in final position for securement to the coronary vessel with stitches or staples.

After removing the balloon 49 and trimming the excess section of the supplying vessel 10, a functional and easy to handle bypassed vessel and coupling apparatus combination 47 is formed. As shown in FIG. 9, this combined apparatus is secured with a pair of forceps and advanced towards the aperture 42 in the target vessel 40. An anastomosis is created by performing a ligation between the coupler apparatus combination 47 and the target vessel 40.

The two objects are secured together by threading stitches through the perforations 34 and the lip of the aperture 42 in the target vessel 10. It is also anticipated by the Applicant that, in this embodiment, the operator can use medical grade staples in place of, or in combination with, the stitches.

Figure 10:
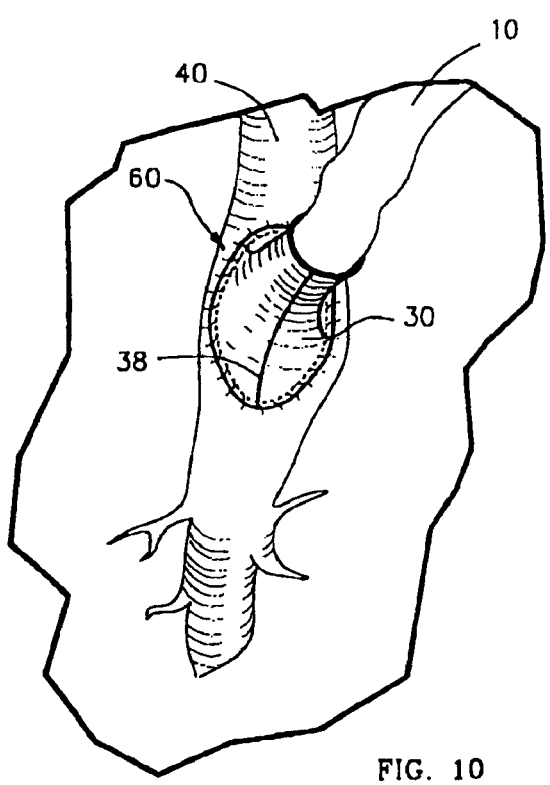
FIG. 10. is a schematic perspective view showing the anastomosis coupling apparatus securing the junction between the severed end of the arterial source and the side-wall of the coronary vessel.

The end result of using the present invention coupler is shown in FIG. 10 (and FIG. 1) whereby the coupler/supplying vessel combination 47 is firmly secured to the aperture 42 of the target vessel 40 to eliminate blood leakage when forming the anastomosis.

Figure 11:
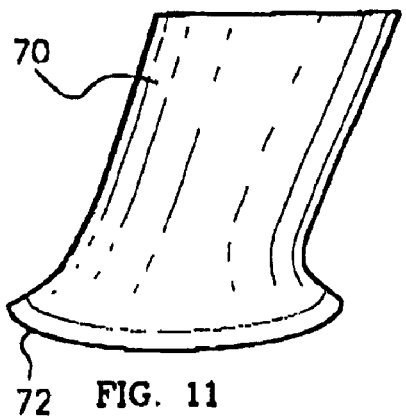
FIG. 11 is a lateral view of second embodiment of an anastomosis coupling apparatus adapted for use in the coronary bypass procedure shown in FIG. 1.
Figure 12:
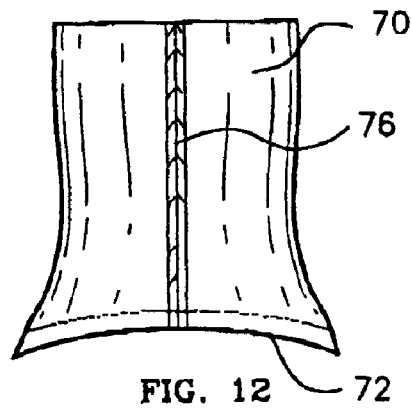
FIG. 12 is a posterior view of the second anastomosis coupling apparatus showing its back hinge mechanism.
Figure 13:
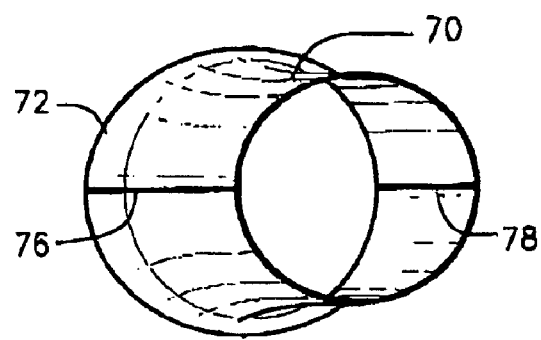
FIG. 13 is an angled superior view of the second anastomosis coupling apparatus.
Figure 14:
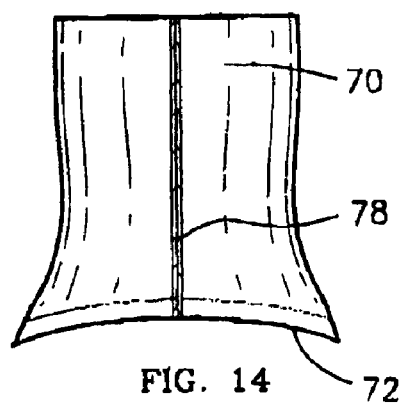
FIG. 14 is an anterior view of the second anastomosis coupling apparatus showing an anterior slot.

Another embodiment of the present coupler invention is demonstrated in FIGS. 11–14. In FIG. 11, the alternate anastomosis coupler apparatus 70 is designed to facilitate a fast and simple means to perform anastomose, which are typically required in minimally invasive bypass procedures. In this embodiment, the apparatus 70 has a wider base 72 which uses only small number of stitches (situation stitches). The primary means for securement is achieved by employing the adhesive techniques described herein. As previously discussed, it can be appreciated that the coupler comprises two halves connected by a hinge mechanism 76 located on the lateral side and separated apart from slot 78 located on anterior side. This "clam shell" design facilitates the proper placement of the supply vessel 10 within the inner cavity defined between the two coupler halves. The by-passing or blood supplying vessel 10 should be positioned so that it exits the lower rim 72 with an elongated shape to fit the shape of the surgically opened aperture of the target coronary vessel.

The hinge mechanism 76 can comprise a simple indent or groove made in the polymer fabrication material, or a more complex arrangement in the metallic design.

Also, proper application of the adhesive or glue to outside surface of the blood supplying vessel and to the inside surface 41 of the anastomosis coupling apparatus 30 is accomplished much easier when separated.

Although a particular form of the invention has been illustrated and described, it will be appreciated by those skilled in the art that various modifications can be made without departing from the spirit and scope of the invention. Accordingly, the scope of the present invention is not to be limited by the particular embodiments above, but is to be defined only by the following claims.

I claim:

1. A method for establishing an end-to-side anastomosis between a severed end of a first hollow organ and a side-wall of a second hollow organ, the method comprising:
    (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
    (b) affixing said input end to said first hollow organ site;
    (c) positioning said output end of said anastomosis coupling apparatus in close proximity with the severed end of said second hollow organ;
    (d) affixing said output end to a severed section of the side-wall of said second hollow organ.

2. A method for establishing an end-to-side anastomosis between a severed end of a first hollow organ and a side-wall of a second hollow organ, the method comprising:
    (a) introducing a specifically configured anastomosis coupling apparatus, having an input end and output end, said coupling apparatus comprising two segments joined together on one side with a hinge mechanism and having a gap on another side for allowing said two segments to be spread apart, said apparatus comprised to engage said severed end of a first hollow organ with said input end and engage said side-wall of a second hollow organ with said output end;
    (b) affixing said output end to a severed section of the side-wall of said second hollow organ;
    (c) positioning said input end of said anastomosis coupling apparatus in close proximity with the site for anastomosis of the first hollow organ;
    (d) affixing said input end to said first hollow organ site.

3. An anastomosis coupling apparatus having an input end, an output end, and comprising two pieces joined on one side by a hinge mechanism and having a gap on another side, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall.

4. An anastomosis coupling apparatus having an input end, an output end, and comprising two pieces joined on one side by a hinge mechanism and having a slot on another side, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said anastomosis coupling is fabricated from a biodegradable material.

5. An anastomosis coupling apparatus having an input end, an output end, and comprising two pieces joined on one side by a hinge mechanism and having a slot on another side, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said anastomosis coupling is fabricated from a biocompatible material.

6. An anastomosis coupling apparatus having an input end, an output end, and comprising two pieces joined on one side by a hinge mechanism and having a slot on another side, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said anastomosis coupling is fabricated from a polymeric material.

7. An anastomosis coupling apparatus having an input end, an output end, and comprising two pieces joined on one side by a hinge mechanism and having a slot on another side, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said anastomosis coupling is fabricated from a metallic material.

8. An anastomosis coupling apparatus having an input end and output end, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said specifically configured anastomosis coupling apparatus has an acute angle between a longitudinal axis of said input end and an longitudinal axis of said output end of said apparatus.

9. The apparatus of claim 8, wherein said acute angle is larger than 5 degrees.

10. An anastomosis coupling apparatus having an input end and output end, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said specifically configured anastomosis coupling apparatus has a right deflection angle between a right angle formed between the longitudinal axis of said input end and an axis parallel to the lip of a distal end of said input end.

11. An anastomosis coupling apparatus having an input end and output end, said apparatus comprised to substantially engage said severed end of a first hollow organ with said input end and substantially engage a side-wall of a second hollow organ with said output end, said coupling apparatus positioning a tissue interface of said first hollow organ in close proximity with a tissue interface of said side-wall, wherein said specifically configured anastomosis coupling apparatus has a lip deflection angle between a right angle formed between the longitudinal axis said input end and an axis parallel the lip of a distal end of said input end.

12. The apparatus of claim 11, wherein said lip deflection angle is larger than 5 degrees.

13. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end further comprising a means for remotely manipulating said anastomosis coupling apparatus for positioning and engaging said coupling apparatus to one of said hollow organs;
   (b) affixing said input end to said first hollow organ;
   (c) positioning said output end of said anastomosis coupling apparatus in close proximity to the side-wall of said second hollow organ;
   (d) affixing said output end to a severed section of the side-wall of said second hollow organ.

14. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
   (b) affixing said input end to said first hollow organ;
   (c) positioning said output end of said anastomosis coupling apparatus in close proximity to a severed section of the side-wall of said second hollow organ;
   (d) affixing said output end to a severed section of the side-wall of said second hollow organ wherein said specifically configured anastomosis coupling is affixed to said severed section by sutures.

15. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
   (b) affixing said input end to said first hollow organ;
   (c) positioning said output end of said anastomosis coupling apparatus in close proximity to the side-wall of said second hollow organ;
   (d) affixing said output end to a severed section of the side-wall of said second hollow organ wherein said anastomosis coupling is affixed to said severed section by staples.

16. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
   (b) affixing said input end to said first hollow organ;
   (c) positioning said output end of said anastomosis coupling apparatus in close proximity to the side-wall of said second hollow organ;
   (d) affixing said output end to a severed section of the side wall of said second hollow organ wherein the adhering of the severed section of the second hollow organ is affixed by applying a biocompatible glue or adhesive.

17. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
   (b) affixing said input end to said first hollow organ;
   (c) positioning said output end of said anastomosis coupling apparatus in close proximity to the side-wall of said second hollow organ;
   (d) affixing said output end to said severed section of said second hollow organ wherein said anastomosis coupling is affixed to said severed section by an any combination of sutures, staples, glue or adhesive.

18. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;
   (b) affixing said input end to said first hollow organ wherein said anastomosis coupling is affixed to said first hollow organ by sutures;
   (c) positioning said output end of said anastomosis coupling apparatus in close proximity to said second hollow organ;
   (d) affixing said output end to a severed section of said second hollow organ.

19. A method for establishing an end-to-side anastomosis between a severed end of a first hollow organ and a side-wall of a second hollow organ, the method comprising:
   (a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end, wherein the first and second hollow organs are both vascular lumens;

(b) affixing said input end to said first hollow organ;

(c) positioning said output end of said anastomosis coupling apparatus in close proximity to said second hollow organ;

(d) affixing said output end to a severed section of said second hollow organ.

20. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end, wherein the first hollow organ is the left internal mammary artery;

(b) affixing said input end to said first hollow organ;

(c) positioning said output end of said anastomosis coupling apparatus in close proximity to said second hollow organ;

(d) affixing said output end to a severed section of said second hollow organ.

21. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end, wherein the second hollow organ is a coronary artery;

(b) affixing said input end to said first hollow organ;

(c) positioning said output end of said anastomosis coupling apparatus in close proximity to said second hollow organ;

(d) affixing said output end to a severed section of said second hollow organ.

22. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;

(b) affixing said input end to said first hollow organ, wherein said anastomosis coupling is affixed to said first hollow organ by sutures;

(c) positioning said output end of said anastomosis coupling apparatus in close proximity to the side-wall of said second hollow organ;

(d) affixing said output end to a severed end of said second hollow organ.

23. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;

(b) affixing said input end to said first hollow organ, wherein said anastomosis coupling is affixed to said first hollow organ by staples;

(c) positioning said output end of said anastomosis coupling apparatus in close proximity to the side-wall of said second hollow organ;

(d) affixing said output end to a severed section of said second hollow organ.

24. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;

(b) affixing said input end to said first hollow organ site, wherein said anastomosis coupling organ is is affixed to said first hollow organ by applying a biocompatible glue or adhesive;

(c) positioning said output end of said anastomosis coupling apparatus in close proximity to the side-wall of said second hollow organ;

(d) affixing said output end to a severed section of said second hollow organ.

25. A method for establishing an end-to-side anastomosis between a severed end of a first hollow organ and a side-wall of a second hollow organ, the method comprising:

(a) introducing an anastomosis coupling apparatus having an input end and output end, said coupling apparatus comprising two pieces joined together with a hinge mechanism located on a posterior side and having an opening slot located on an anterior side, said apparatus comprised to engage said severed end of a first hollow organ with said input end and engage said side-wall of a second hollow organ with said output end;

(b) affixing said input end to said first hollow organ, wherein said anastomosis coupling is affixed to said severed end by an any combination of sutures, staples, glue or adhesive;

(c) positioning said output end of said anastomosis coupling apparatus in close proximity to the side-wall of said second hollow organ;

(d) affixing said output end to a severed section of said second hollow organ.

26. A method for establishing an end-to-side anastomosis between a severed end of a first hollow organ and a side-wall of a second hollow organ, the method comprising:

(a) introducing a specifically configured anastomosis coupling apparatus, having an input end and output end, said coupling apparatus comprising two segments joined together on one side with a hinge mechanism and having a gap on another side for allowing said two segments to be spread apart, said apparatus comprised to engage said severed end of a first hollow organ with said input end and engage said side-wall of a second hollow organ with said output end;

(b) affixing said output end to the side-wall of said second hollow organ;

(c) positioning said input end of said anastomosis coupling apparatus in close proximity with the site for anastomosis of the first hollow organ;

(d) affixing said input end to said first hollow organ site, wherein the first hollow organ is the left internal mammary artery.

27. A method for establishing an end-to-side anastomosis between a severed end of a first hollow organ and a side-wall of a second hollow organ, the method comprising:

(a) introducing a specifically configured anastomosis coupling apparatus, having an input end and output end, said coupling apparatus comprising two segments joined together on one side with a hinge mechanism and having a gap on another side for allowing said two segments to be spread apart, said apparatus comprised to engage said severed end of a first hollow organ with said input end and engage said side-wall of a second hollow organ with said output end;

(b) affixing said output end to the side-wall of said second hollow organ, wherein the second hollow organ is a coronary artery;

(c) positioning said input end of said anastomosis coupling apparatus in close proximity with the site for anastomosis of the first hollow organ;

(d) affixing said input end to said first hollow organ site.

28. A method for establishing an end-to-side anastomosis between a severed end of a first hollow organ and a side-wall of a second hollow organ, the method comprising:

(a) introducing a specifically configured anastomosis coupling apparatus, having an input end and output end, said coupling apparatus comprising two segments joined together on one side with a hinge mechanism and having a gap on another side for allowing said two segments to be spread apart, said apparatus comprised to engage said severed end of a first hollow organ with said input end and engage said side-wall of a second hollow organ with said output end, wherein the first and second hollow organs are both vascular lumens;

(b) affixing said output end to the side-wall of said second hollow organ;

(c) positioning said input end of said anastomosis coupling apparatus in close proximity with the site for anastomosis of the first hollow organ;

(d) affixing said input end to said first hollow organ site.

29. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end an output end, and a hinge mechanism on one side and a opening slot on another side, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ.

30. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end an output end, and a hinge mechanism on one side and a opening slot on another side, wherein said specifically configured anastomosis coupling is fabricated from a biodegradable material, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ.

31. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end an output end, and a hinge mechanism on one side and a opening slot on another side, wherein said specifically configured anastomosis coupling is fabricated from a biocompatible material, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ.

32. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end an output end, and a hinge mechanism on one side and a opening slot on another side, wherein said specifically configured anastomosis coupling is fabricated from a polymeric material, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ.

33. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end an output end, and a hinge mechanism on one side and a opening slot on another side, wherein said specifically configured anastomosis coupling is fabricated from a metallic material, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ.

34. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ wherein said specifically configured anastomosis coupling is affixed to said severed end by sutures.

35. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ wherein said specifically configured anastomosis coupling is affixed to said severed end by staples.

36. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ;

(b) affixing a first end of said anastomosis coupling apparatus to a first hollow organ, wherein the adhering of a severed end of the first hollow organ is effectuated by applying a biocompatible glue or adhesive;

(c) affixing a second end of said anastomosis coupling apparatus to a second hollow organ.

37. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ wherein said specifically configured anastomosis coupling is affixed to said severed end by an any combination of sutures, staples, glue or adhesive.

38. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ;

(b) affixing a first end of said anastomosis coupling apparatus to a first hollow organ;

(c) affixing a second end of said anastomosis coupling apparatus to a second hollow organ wherein said specifically configured anastomosis coupling is affixed to said severed end by sutures.

39. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end, an output end, and a hinge mechanism on one side and a opening slot on another side, said apparatus comprised to secure a first hollow organ to a second hollow organ, wherein the first hollow organ is the left internal mammary artery;

(b) affixing a first end of said anastomosis coupling apparatus to a first hollow organ;

(c) affixing a second end of said anastomosis coupling apparatus to a second hollow organ.

40. A method for performing a coronary bypass by establishing an end-to-side anastomosis between an arterial source of oxygenated blood and a coronary artery having a stenosis, the method comprising:

(a) introducing a specifically configured anastomosis coupling apparatus having an input end and output end, said apparatus comprised to secure a first hollow organ to a second hollow organ, wherein said specifically configured anastomosis coupling apparatus has an acute angle between a longitudinal axis of said input end and an longitudinal axis of said output end of said apparatus;

(b) affixing a first end of said anastomosis coupling apparatus to a first hollow organ; and (c) affixing a second end of said anastomosis coupling apparatus to a second hollow organ.

41. The method of claim 40, wherein said acute angle is larger than 5 degrees.

42. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end and output end, said apparatus comprised to secure a first hollow organ to a second hollow organ, wherein said specifically configured anastomosis coupling apparatus has a right deflection angle between a right angle formed between the longitudinal axis of said input end and an axis parallel to the lip of a distal end of said input end;

(b) affixing a first end of said anastomosis coupling apparatus to a first hollow organ; and (c) affixing a second end of said anastomosis coupling apparatus to a second hollow organ.

43. The method of claim 42, wherein said right deflection angle is larger than 5 degrees.

44. A method for performing a coronary bypass by establishing an end-to-side anastomosis between an arterial source of oxygenated blood and a coronary artery having a stenosis, the method comprising:

(a) introducing a specifically configured anastomosis coupling apparatus, having an input end and output end, said apparatus comprised to secure a first hollow organ to a second hollow organ, wherein said specifically configured anastomosis coupling apparatus has an lip deflection angle between a right angle formed between the longitudinal axis of said input end and an axis parallel the lip of a distal end of said input end;

(b) affixing a first end of said anastomosis coupling apparatus to a first hollow organ; and (c) affixing a second end of said anastomosis coupling apparatus to a second hollow organ.

45. The method of claim 44, wherein said lip deflection angle is larger than 5 degrees.

46. An anastomosis coupling apparatus, said coupling apparatus having an input end, and output end, a hinge mechanism on one side and a gap on another side, said apparatus comprised to substantially engage a severed end of a first hollow organ with said input end and substantially engage a side-wall of a second hollow organ with said output end.

47. The apparatus of claim 46, wherein said hinge mechanism allows said coupling apparatus to open said gap to attain an open configuration for positioning and securing said severed end of said first hollow organ within said input end.

48. The apparatus of claim 46, where said hinge mechanism allows said coupling apparatus to close said gap and attain a closed configuration that substantially engages said severed end of said first hollow organ within said input end.

* * * * *